United States Patent [19]
Kaiser

[11] Patent Number: 5,569,187
[45] Date of Patent: Oct. 29, 1996

[54] METHOD AND APPARATUS FOR WIRELESS CHEMICAL SUPPLYING

[75] Inventor: Ulrich Kaiser, Warstein, Germany

[73] Assignee: Texas Instruments Incorporated, Dallas, Tex.

[21] Appl. No.: 291,257

[22] Filed: Aug. 16, 1994

[51] Int. Cl.$^6$ .................................................. A61M 31/00
[52] U.S. Cl. ............................................................. 604/67
[58] Field of Search ........................... 604/30–34, 65–67, 604/890.1, 891.1, 892.1, 250–255

[56] References Cited

U.S. PATENT DOCUMENTS

| | | | |
|---|---|---|---|
| 3,921,916 | 11/1975 | Bassous | 239/601 |
| 4,007,464 | 2/1977 | Bassous et al. | 346/75 |
| 4,282,872 | 8/1981 | Franetzki et al. | 128/213 |
| 4,333,072 | 6/1982 | Beigel | 340/825.54 |
| 5,041,826 | 8/1991 | Milheiser | 340/825.54 |
| 5,053,774 | 10/1991 | Schuermann et al. | 342/44 |

OTHER PUBLICATIONS

R. G. Sweet, "*High Frequency Recording with Electrostatically Deflected Ink Jets*", The Review of Scientific Instruments, vol. 36, No. 2, Feb. 1965, pp. 131–136.

F. J. Kamphoefner, "*Ink Jet Printing*", IEEE Transactions on Electron Devices, vol. ED–19, No. 4, Apr. 1972, pp. 584–593.

IBM Journal of Research and Development, vol. 21, No. 1, Jan. 1977, pp. 1–80.

R. D. Carnahan and S. L. Hou, "*Ink Jet Technology*", IEEE Transactions on Industry Applications, vol. 1A–13, No. 1, Jan./Feb. 1977, pp. 95–105.

L. Kuhn, E. Bassous, and R. Lane, "*Silicon Charge Electrode Array for Ink Jet Printing*", IEEE Transactions on Electron Devices, vol. ED–25, No. 10, Oct. 1978, pp. 1257–1260.

K. E. Petersen, "*Fabrication of an integrated, Planar Silicon Ink–Jet Structure*", IEEE Transactions on Electron Devices, vol. ED–26, No. 12, Dec. 1979, pp. 1918–1920.

K. E. Petersen, "*Silicon as a Mechanical Material*", Proceedings of the IEEE, vol. 70, No. 5, May 1982, pp. 420–457.

*Primary Examiner*—Manuel Mendez
*Attorney, Agent, or Firm*—Rebecca A. Mapstone; James C. Kesterson; Richard L. Donaldson

[57] ABSTRACT

A method and apparatus for wireless supplying of chemicals is provided in which an interrogation unit (14) transmits interrogation signals. A responder unit (16), powered from the interrogation signals, is operable to receive the interrogation signals and transmit responses. The responder unit (16) controls operation of an actuator (10). The actuator is coupled to a supply tank (12), which supplies chemicals under control of the actuator (10).

20 Claims, 2 Drawing Sheets

METHOD AND APPARATUS FOR WIRELESS CHEMICAL SUPPLYING

TECHNICAL FIELD OF THE INVENTION

This invention relates in general to the field of electronic devices, and more particularly to a method and apparatus for wireless supply of chemicals.

BACKGROUND OF THE INVENTION

In many chemical supply systems, the amount of chemicals disbursed from the system must be strictly controlled. Supply of chemicals is normally controlled by valves. Often, a control system operates an actuator that changes or maintains the valve position. For example, the medical field frequently uses control systems, which operate actuators and valves, to control the supply of various drugs. This chemical supply equipment must frequently be placed in aggressive environments. As a result, the supply of chemicals may be inhibited and acquisition of data related to the chemical supply may be inaccurate. In addition, the chemical supply system could be subject to corrosion or other damage in these aggressive environments.

Another source of problems with present chemical sensor systems is the wiring itself. For example, noise may be introduced into the supply system due to noise induction in the wiring between the chemical supply and the control circuitry. In addition, the use of wiring tends to result in no galvanic separation, which may cause ground loops or isolation problems.

Another problem with typical chemical supply systems results when the supply of chemicals is controlled by battery. Batteries result in large and costly systems. Furthermore, the chemical supply systems must be frequently accessed to maintain operation by changing the battery.

Furthermore, another problem results when attempting to build a chemical supply system in which control circuitry must be multiplexed between multiple chemical supplies. Such systems require control circuitry to be physically moved between different chemical supplies to effectively multiplex the equipment. This results in an inconvenience to the user of the chemical supply system. In addition, other problems may result due to the need to constantly detach and reattach control equipment when multiplexing chemical supplies.

SUMMARY OF THE INVENTION

Therefore, a need has arisen to provide a low-cost chemical supply system that eliminates wiring in an aggressive chemical environment and permits multiplexing of control circuitry. Specifically, a need has arisen for a wireless chemical supply system that operates without batteries and is addressable.

Furthermore, a need has arisen to operate multiple chemical supplies that permit individual addressing by a single piece of control circuitry.

In accordance with the teachings of the present invention, a method and apparatus for wireless supply of chemicals are provided that substantially eliminate or reduce disadvantages and problems associated with prior chemical supply systems. In particular, a chemical supply system for wireless supply of chemicals is provided. An interrogation unit operates to transmit interrogation signals and receive responses. A responder unit, which is powered from the interrogation signals, receives interrogation signals and transmits responses to the interrogation unit. Under control of the responder unit, an actuator receives control signals. The actuator controls supply of chemicals from a supply tank.

A particular application for the wireless chemical supply system involves the use of a plurality of supply tanks. A single interrogation unit is operable to transmit interrogation signals and receive responses from responder units associated with each supply tank. Each supply tank operates under control of an actuator, which receives control signals from its corresponding responder unit.

Furthermore, the interrogation unit is operable to transmit interrogation signals with at least some of the interrogation signals including individual addresses. Each of the responder units has a demodulator for demodulating the interrogation signals into addresses, and a processor for comparing demodulated addresses with the responder unit address. Enabling circuitry is provided in each responder unit to enable the unit to respond only when the demodulated address matches the responder unit address. Therefore, a plurality of chemical supplies, each associated with a separate actuator and responder unit, can respond to a single interrogation unit.

According to another aspect of the present invention, a method for a wireless supply of chemicals is provided. The method includes the step of transmitting an interrogation signal from an interrogation unit to a responder unit. The responder unit receives the interrogation signal, which provides the responder unit with power. The actuator operates under control of the responder unit and supplies chemicals from a supply tank.

An important technical advantage of the present invention is the fact that the wireless chemical supply system can supply chemicals conveniently and inexpensively. In addition, the responder unit is capable of measuring and keeping track of the amount of chemical supplied. In addition, the chemical supplies associated with the responder units do not require a local battery or other power supply. Instead, the responder units and chemical supplies are powered from interrogation signals received from the interrogation unit.

Furthermore, another important aspect of the present invention is the ability to eliminate wire connections between a chemical supply, an actuator, and the related control circuitry. By eliminating wire connections, significant reductions in noise interference are obtained. In addition, another advantage exists in the ability to multiplex control circuitry by supplying each responder unit with an individual address.

BRIEF DESCRIPTION OF THE DRAWINGS

For a more complete understanding of the present invention and the advantages thereof, reference is now made to the following description taken in conjunction with the accompanying drawings in which like reference numbers indicate like features and wherein.

DETAILED DESCRIPTION OF THE INVENTION

Figure 1:
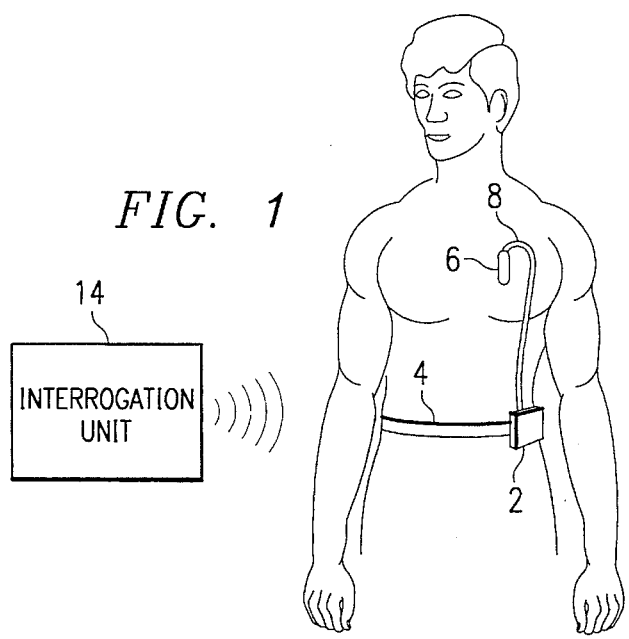
FIG. 1 is an illustration of the wireless chemical supply system of the present invention being worn by a patient.

FIG. 1 illustrates an application involving a patient using a wireless chemical supply system according to the present invention. A supplemental supply tank 2 may also be provided, and in a particular application may be attached to the patient by a strap 4. A wireless chemical supply, indicated generally at 6, is implanted in the body to supply chemicals. According to one embodiment of the present invention, the chemical supply system is operable to provide insulin. It should be understood that other medical applications and non-medical applications are available. The supply of insulin is presented solely as an exemplary embodiment to teach the advantages of the present invention.

As shown in FIG. 1, a tube 8 provides the chemicals from the supplemental tank 2 to the wireless chemical supply 6. As will be discussed below, an interrogation unit 14 transmits control signals to the wireless chemical supply system. The control signals operate to control the supply of chemicals from the wireless chemical supply 6. Furthermore, the interrogation unit 14 may receive information from the wireless chemical supply system.

It should be understood that implanting the wireless chemical supply in a human being and the inclusion of a supplemental tank are presented solely for exemplary purposes. Other applications are available according to the present invention. For example, the wireless chemical supply system may be used in any environment in which the supply of chemicals must be controlled, but it is impractical to locate the wiring and control circuitry in that environment, because of electromagnetic noise, or aggressive chemical environments, for example.

Figure 2:
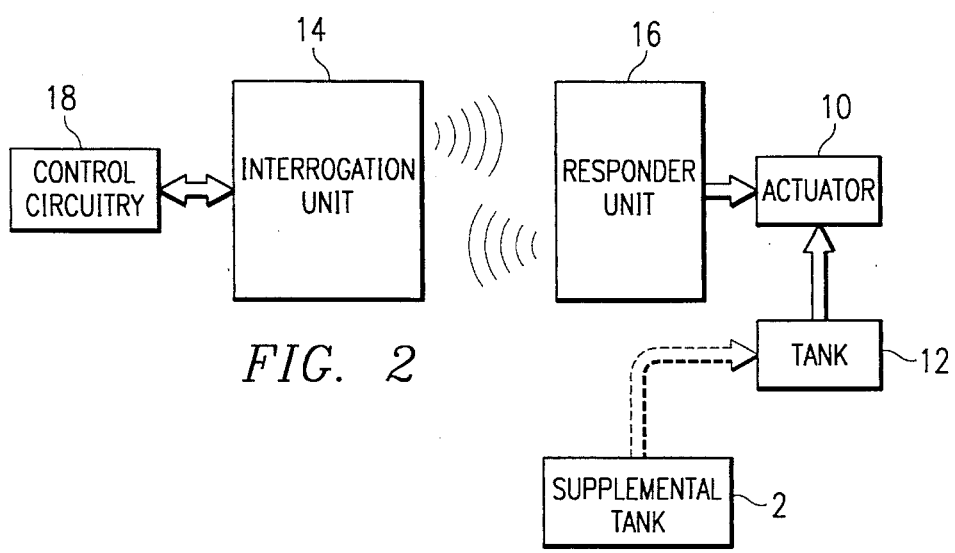
FIG. 2 is a block diagram illustrating communications between an interrogation unit and a responder unit according to the teachings of the present invention.

FIG. 2 illustrates a wireless chemical supply system according to the present invention. As illustrated in FIG. 2, an actuator (or pump) 10 is coupled to a chemical supply tank 12. The supply of chemicals from the tank 12 is controlled by the operation of actuator 10. According to one embodiment of the present invention, the actuator 10 comprises a piezoelectric pressure oscillator operable to pump chemicals from the supply tank 12. However, it should be understood that the selection of a piezoelectric pressure oscillator is exemplary only. Other actuators may be used in accordance with the present invention. For example, the supply tank 12 may be pressurized, such as at manufacture, and the actuator 10 may be a valve, or a valve and pump. Many such combinations are contemplated herein.

The supply tank 12 and actuator 10 are coupled to a responder unit 16. The responder unit 16 is operable to control the amount of chemicals supplied by the actuator 10 from the chemical supply tank 12. In addition, responder unit 16 is operable to transmit data to interrogation unit 14. For example, the responder unit 16 may transmit data concerning the amount of chemicals supplied by the chemical supply tank 12 and actuator 10, or simply an acknowledgement that it has received its control signals or performed its supply, among other responses. The interrogation unit 14 receives this data from responder unit 16 and either processes and stores the data locally or provides this data to control circuitry 18. In addition to receiving data, control circuitry 18 operates to supply control data to interrogation unit 14 to be transmitted to responder unit 16. Control circuitry 18 may be, for example, a processor based control system, such as a personal computer, among other possible control systems. The responder unit 16 controls the supply of chemicals from tank 12 and actuator 10 based on the received control data. It should be understood that interrogation unit 14 may be programmed to perform without the need for control circuitry 18.

In another embodiment of the present invention, the supplemental tank 2 is coupled to the chemical supply tank 12. In operation, the supplemental tank 2 supplies additional chemicals to tank 12 when the capacity of tank 12 is insufficient.

Figure 3:
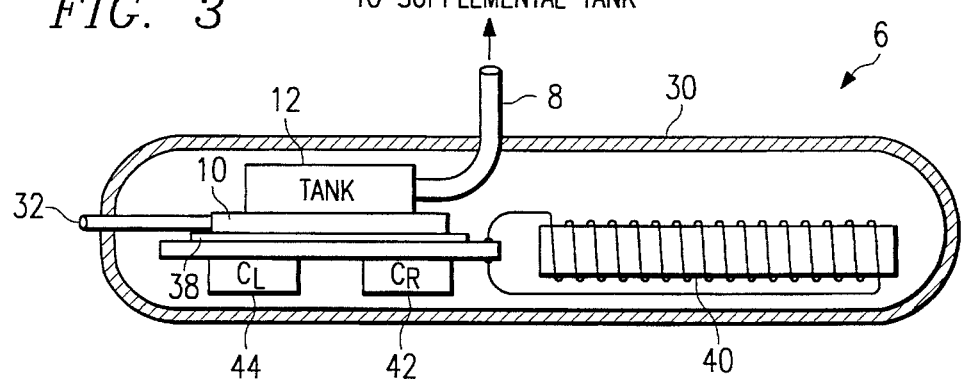
FIG. 3 is a diagram of the integration of a chemical supply tank, an actuator, and a responder unit in a housing according to the teachings of the present invention.

FIG. 3 illustrates a particular embodiment of the wireless chemical supply system comprising a responder unit 16, an actuator 10, and a tank 12. A housing 30 is provided to contain the wireless chemical supply system. Such a housing provides an important technical advantage of the present invention because chemical supplies are often placed in aggressive or hostile environments. In these environments, responder unit 16, chemical tank 12, and actuator 10 could potentially be damaged. Therefore, the housing 30 prevents corrosion and other adverse effects upon the wireless chemical supply system. In a particular embodiment of the present invention, the housing 30 is comprised of glass. However, it should be understood that the use of glass is exemplary only and that other materials that protect the wireless chemical supply system may also be used for the housing without departing from the intended scope of the present invention.

As shown in FIG. 3, the tank 12 operates under the control of actuator 10. The actuator 10 operates as a small pump that forces chemicals stored in tank 12 through opening 32 to supply chemicals external to the housing 30. The tank 12 and actuator 10 are coupled to integrated circuit 38. In one embodiment of the present invention, the integrated circuit 38 comprises the responder unit 16. It should be understood that the use of the integrated circuit in FIG. 3 is exemplary only. Other configurations may be used in which the responder unit 16 and actuator 10 comprise a single integrated circuit. In addition, the responder unit 16 and actuator 10 can further be combined with the tank 12 in a single integrated circuit. In another embodiment of the present invention, the nozzle 32, tank 12, and responder unit 16 are combined in a single integrated circuit using silicon planar processing methods. It should be understood, however, that other methods are available to integrate a responder unit 16, tank 12, and actuator 10 in a single integrated circuit. For example, anisotropic etching, which is a common processing method for ink jet printing technology, can be used to integrate these elements.

For examples of fabrication techniques, see K. E. Peterson, "Silicon as a Mechanical Material," Proceedings of the IEEE, Vol. 70, No. 5, May 1982, pp. 420–457, and cited reference articles, particularly references 81–88. These references are herein incorporated by reference.

In FIG. 3, the responder unit 16 communicates with interrogation unit 14 through the use of radio frequency ("RF") waves. With this approach, wireless, contactless control of the chemical supply tank 12 may be accomplished. Such communication provides an important technical advantage of the present invention, since control of the chemical supply may be performed conveniently and quickly. In addition, the wireless and contactless control of the chemical supply eliminates or reduces noise problems in the chemical sensor system.

The reception of the RF interrogation signal at the responder unit 16 is performed by a parallel resonant circuit having a coil 40 and a capacitor 42. Coupled to the parallel resonant circuit is a capacitor serving as an energy accumulator 44. Typically, this capacitor is coupled to a $V_{cc}$ pad and a ground pad. The resonant circuit is also coupled to the $V_{cc}$ pad. The resonant circuit receives an interrogation signal and the energy from that signal is stored in the energy accumulator 44. The energy stored from the signal is used to operate the responder unit 16 and actuator 10.

In operation, the circuit in FIG. 3 may be used to supply chemicals in hostile environments. For example, the wireless chemical supply may be implanted in a patient to supply insulin. Control circuitry 18 provides information to an interrogation unit 14 to control the supply of chemicals. The interrogation unit 14 communicates with responder unit 16. The responder unit 16 receives the control circuit data and controls operation of actuator 10. The actuator 10 pumps small amounts of chemical from tank 12 through nozzle 32. The responder unit 16 may measure the amount of chemical supplied from tank 12 and transmit this data to control circuitry 18 by communicating with interrogation unit 14. In addition, another embodiment of the particular invention permits the hose 8 to connect to the supplemental tank 2. It should be understood, however, that the use of a supplemental tank 2 is for exemplary purposes only. The present invention may or may not use a supplemental tank. With a supplemental tank 2 and hose 8, a one-way valve may be included between the supplemental tank 2 and the tank 12, to provide a pressure compensation for the actuator 10.

Figure 4:
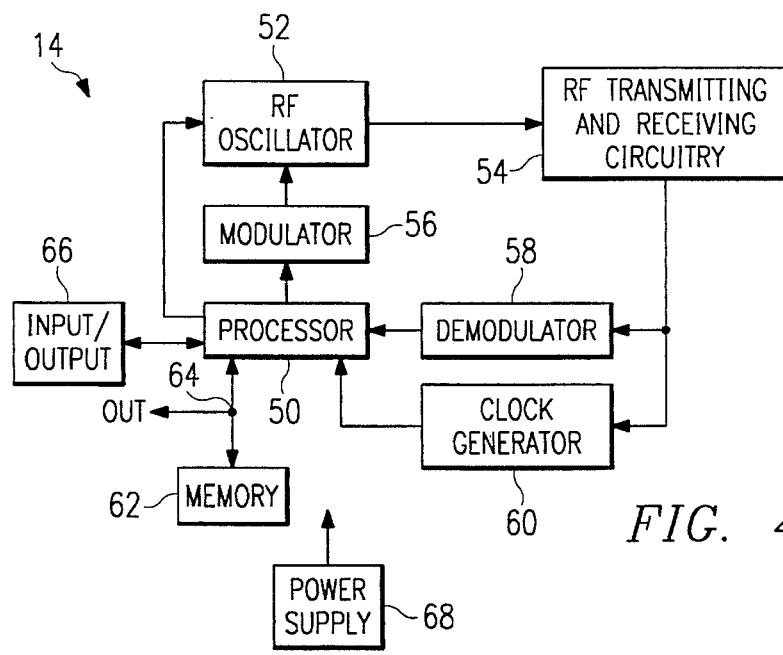
FIG. 4 is a block diagram of an interrogation unit according to the teachings of the present invention.

FIG. 4 illustrates a block diagram of interrogation unit 14 according to the teachings of the present invention. As shown in FIG. 4, a processor 50 controls RF oscillator 52. RF oscillator 52 generates an output that is coupled to RF transmitting and receiving circuitry 54. In a particular embodiment, RF oscillator 52 may operate at a nominal frequency of 125 kHz or 134.2 kHz. Processor 50 is also coupled to a modulator 56 that may be used to modulate the frequency (or amplitude or phase) of the output of RF oscillator 52. RF transmitting and receiving circuitry 54 is also coupled to demodulator 58 and clock generator 60. Demodulator 58 and clock generator 60 are coupled to processor 50. Processor 50 stores information received from demodulator 58 into memory 62.

Data from memory 62 or processor 50 may also be output to an external control circuitry 18 through output 64. Similarly, data can be output to input/output device 66 as shown in FIG. 4. Input/output device 66 may also be used to initiate operation of the interrogation unit 14. Input/output device 66 may also comprise a display, on which information received from the wireless chemical supply may be displayed. A power supply 68 is provided for powering interrogation unit 14. Power supply 68 may be a rechargeable battery, non-rechargeable battery, or other power supply. In operation, interrogation unit 14 will be activated to supply control information to the remote responder unit 16. RF transmitting and receiving circuitry 54 transmits an interrogation signal and control information. Sometime thereafter, transmitting and receiving circuitry 54 receives a response from responder unit 16. This response is input to clock generator 60 and demodulator 58. Clock generator 60 generates a clock based on the returned signal. Furthermore, demodulator circuit 58 demodulates the response. For example, the response may have been modulated using frequency-shift keying ("FSK"). Thus, a response at a particular frequency for a given amount of time will be recognized as a "0" and a received signal at another frequency received for a given amount of time will be recognized as a "1." Processor 50 will read this data and store it to memory 62. In addition, the data may also be output at output 64 or to input/output device 66.

In addition, it may be desirable to individually address a plurality of chemical actuators 10 and tanks 12 being used to supply chemicals in various chemical environments. With individual addressing, a single interrogation unit 14 permits a single control circuit 18 to be multiplexed to access multiple chemical actuators 10 and tanks 12. The ability to access multiple chemical actuators 10 and tanks 12 with a single interrogation unit provides an important technical advantage of the present invention. The use of a single control circuit 18 prevents inconvenience or other potential problems associated with detaching and reattaching data acquisition equipment to different chemical actuators 10 and supply tanks 12.

In an embodiment of the present invention, modulator 56 is provided to permit access to multiple chemical actuators 10 and supply tanks 12. In particular, the frequency (or amplitude or phase) of the output of the RF oscillator 52 is modulated by modulator 56, which is controlled by processor 50. In this way, an interrogation signal generated by RF transmitting and receiving circuitry 54 will be modulated according to the particular address of the particular chemical actuator 10 and supply tank 12 to be controlled. Thus, a responder unit 16 will respond to an interrogation signal only when the demodulated address corresponds to the predefined responder unit address. Upon detecting the proper responder unit address, the responder unit 16 receives control information, which controls operation of the chemical actuator 10 and supply 12, from interrogation unit 14.

A particular embodiment of interrogation unit 14 is described in U.S. Pat. No. 5,053,774 entitled "Transponder Arrangement" and issued on Oct. 1, 1991. That patent is herein incorporated by reference.

Figure 5:
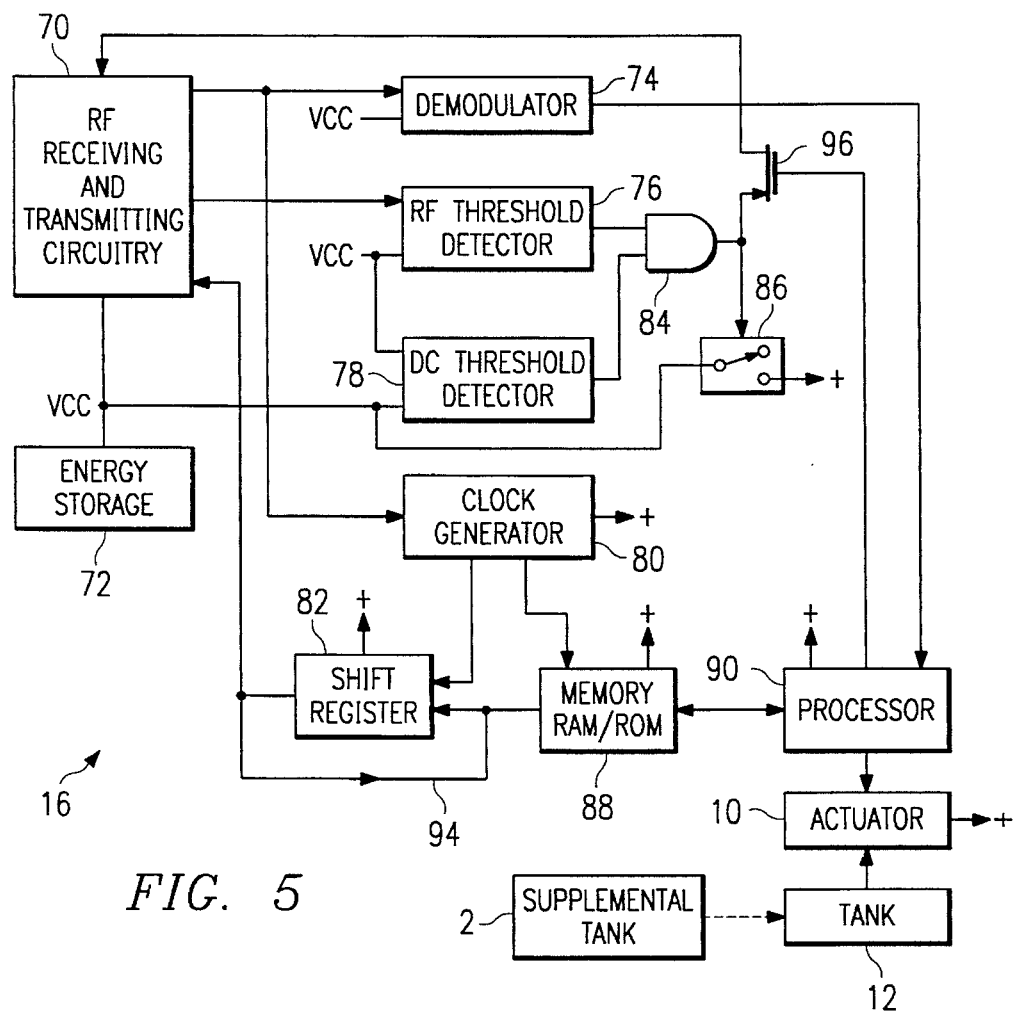
FIG. 5 is a block diagram of a responder unit according to the teachings of the present invention.

FIG. 5 illustrates a block diagram of a responder unit 16 according to the teachings of the present invention. As shown in FIG. 5, RF receiving and transmitting circuitry 70 is coupled to an energy storage 72, demodulator 74, RF threshold detector 76, DC threshold detector 78, clock generator 80, and shift register 82. The RF receiving and transmitting circuitry 70 is operable to receive and transmit data via RF frequencies between the interrogation unit 14 and the responder unit 16. RF threshold detector 76 and DC threshold detector 78 are coupled to an AND-Gate 84. The output of AND-Gate 84 controls a switch 86, which is used to couple power from energy storage 72 to clock generator 80 and shift register 82. The output of AND-Gate 84 is also coupled to circuitry 70 (as shown, through a switch 96 to be discussed, which is included for individual addressing). Also, the output of switch 86 is coupled to a memory 88, a processor 90, and an actuator 10. The memory 88 is coupled to processor 90, clock generator 80, and shift register 82. The processor 90 is also coupled to demodulator 74 and actuator 10. Actuator 10 is used to control the disbursement of chemicals from chemical tank 12.

In operation, RF receiving and transmitting circuitry 70 receives an interrogation signal from interrogation unit 14. As a signal is received, energy is stored in energy storage 72, which may comprise a capacitor. At the end of the interrogation signal, RF threshold detector 76 will detect a decreased received RF energy, and will output a signal to AND-Gate 84. As discussed above, the received energy from the RF interrogation signal is stored in energy storage 72. Energy storage 72 will be used to power all of the circuitry within responder unit 16. Thus, no local battery or other power supply is needed for responder unit 16. This provides an important technical advantage since a responder unit 16 will require no maintenance to replace batteries, which may be required in other chemical supply systems.

Once the energy level within energy storage 72 reaches a level sufficient to power each of the devices within responder unit 16, DC threshold detector 78 will also output a signal to AND-Gate 84. Once the outputs from both detector 76 and detector 78 are received by AND-Gate 84, switch 86 will be activated, thus powering the other circuitry on responder unit 16. Furthermore, it should be noted that the energy storage 72 may also be used to power actuator 10.

The output of AND-Gate 84 is also coupled to RF receiving and transmitting circuitry 70 and triggers the transfer of energy from energy storage 72 through circuitry 70 to generate an RF carrier signal to be transmitted back to interrogation unit 14. This RF carrier signal is also used to generate clock signals through clock generator 80. Clock generator 80 controls shift register 82 and memory 88 such that data stored in memory 88 is transferred to shift register 82. The data output from shift register 82 is transmitted to RF receiving and transmitting circuitry 70. This output is used to modulate the RF carrier wave output by circuitry 70. For example, the bits output by shift register 82 may be used to cause FSK modulation of the RF carrier wave output by circuitry 70. Shift register 82 may also include a feedback loop 94. Feedback loop 94 will be used once all data to be transmitted are loaded within shift register 82. These bits will then be reloaded into the shift register as they are shifted out, so that the data to be transmitted to interrogation unit 14 may be retransmitted without needed to reaccess memory 88.

In another embodiment of the present invention, the amount of chemical supplied by tank 12 is measured by processor 90. Processor 90 loads the data concerning the amount of chemical supplied into memory 88. Memory 88 may be a combination of random access memory, read-only memory, or EEPROM. The particular address of the responder unit 16 may be included in the ROM or EEPROM portion of memory 88. The RAM portion of memory 88 will store the particular data measured by processor 90. The address and data will then be loaded from memory 88 to shift register 82. It should be noted, however, that address and data need not be included in all applications of the present invention. Configuring the responder unit 16 to respond to the interrogation unit 14 with address and data is exemplary only. Other embodiments of the present invention may or may not include circuitry to respond to interrogation unit 16. For example, responder unit 16 could be configured to only receive control information from interrogation unit 16.

In addition, FIG. 5 illustrates the circuitry required to perform addressing of multiple chemical supply tanks 12 and actuators 10. The demodulator circuit 74 demodulates signals from interrogation unit 14. The output of demodulator 74 is input to processor 90. Processor 90 compares the information demodulated by demodulator 74 with address data stored in memory 88. If the demodulated address from demodulator 74 corresponds to the address stored in memory 88, then the particular responder unit 16 and chemical supply tank 12 have been addressed. If the data does not match, then the particular responder unit has not been addressed and will not respond. When individual addressing of responder unit 16 is desired, the output of AND-Gate 84, which is coupled to RF receiving and transmitting circuitry 70 will pass through a switch 96. Switch 96 is controlled by processor 90. Switch 96 will be closed only if the address received from interrogation unit 14 corresponds to the address of responder unit 16. With the switch 96 open, no response is enabled. Thus, the switch 96 and processor 90 operate as enabling circuitry. The enabling circuitry presents an important technical advantage of the present invention. Through the enabling circuitry and addressing capabilities, a single control circuit and interrogation unit may operate to multiplex multiple chemical supply tanks 12 and actuators 10.

The processor 90 may be a programmable microprocessor. However, the use of a microprocessor is exemplary only. Other processing units may be used without departing from the intended scope of the present invention, including a microcontroller, a programmable array logic, gate array logic, or any other circuitry capable of performing logic and control functions discussed herein.

A particular embodiment for responder unit 16 is disclosed in U.S. Pat. No. 5,053,774, entitled "Transponder Arrangement" and issued on Oct. 1, 1991. That patent is herein incorporated by reference.

Although the present invention has been described in detail, it should be understood that various changes, substitutions, and alterations can be made without departing from the intended scope as defined by the appended claims.

What is claimed is:

1. A wireless chemical supply system, comprising:
   an interrogation unit operable to transmit interrogation signals and receive responses;
   a responder unit, being powered from said interrogation signals, said responder unit operable to receive said interrogation signals and transmit responses to said interrogation signals;
   an actuator coupled to said responder unit, said actuator operable to receive control signals from said responder unit; and
   a supply tank operatively coupled to said actuator, said supply tank operable to supply chemicals under control of said actuator.

2. The system of claim 1, wherein said actuator and said responder unit comprise a single integrated circuit.

3. The system of claim 1, wherein said actuator, said responder unit, and said supply tank comprise a single integrated circuit.

4. The system of claim 1, wherein said responder unit further comprises a processor operable to monitor and control the amount of chemical supplied from said supply tank.

5. The system of claim 1, further comprising a supplemental supply tank, wherein said supplemental supply tank is operatively coupled to said supply tank for providing said supply tank additional chemicals.

6. The system of claim 1, wherein said actuator comprises a piezoelectric pressure oscillator operable to pump chemicals from said supply tank.

7. The system of claim 1, wherein said actuator comprises a valve, and wherein said supply tank is pressurized.

8. The system of claim 1, wherein the wireless chemical supply is operable to supply insulin.

9. The system of claim 1, further comprising a control circuit, said control circuit operatively coupled to said interrogation unit, said control circuit operable to provide control data to said interrogation unit for transmission to said responder unit.

10. A wireless chemical supply system, comprising:
   an interrogation unit operable to transmit and receive interrogation signals and receive responses;
   a plurality of supply tanks each operable to supply chemicals;
   a plurality of actuators, one each of said actuators associated with one each of said supply tanks, said actuators operable to control supply of chemicals from said supply tanks;

a plurality of responder units, one each of said responder units associated with one each of said actuators and one each of said supply tanks, said responder units being powered from said interrogation signals, said responder units operable to receive said interrogation signals, control operation of said actuators, and transmit responses to said interrogation signals.

11. The system of claim 10, wherein at least one of said actuators and associated responder unit comprise a single integrated circuit.

12. The system of claim 10, wherein at least one of said actuators and associated supply tank and responder unit comprise a single integrated circuit.

13. The system of claim 10, wherein at least one of said responder units further comprises a processor operable to monitor and control the amount of chemical supplied from said supply tank associated with said responder unit.

14. The system of claim 10, further comprising a plurality of housings, wherein at least one of said responder units and associated supply tank and actuator are substantially disposed within one each of said associated housings.

15. The system of claim 10, further comprising a plurality of supplemental supply tanks, wherein at least one of said supply tanks is operatively coupled to one each of said supplemental supply tanks.

16. The system of claim 10, wherein said interrogation unit is operable to modulate said interrogation signal to provide individual responder unit addressing, and wherein each of said responder units comprises:

a demodulator operable to demodulate interrogation signals into addresses;

a processor coupled to said demodulator and operable to compare the demodulated addresses with a responder unit address; and enabling circuitry operable to enable said responder unit when said demodulated address matches said responder unit address.

17. A method for wireless supply of chemicals, comprising:

transmitting an interrogation signal from an interrogation unit to a responder unit, the responder unit associated with a supply tank and an actuator;

receiving the interrogation signal at the responder unit;

powering the responder unit from the interrogation signal;

operating the actuator under control of the responder unit; and supplying chemicals from the supply tank under control of the actuator.

18. The method of claim 17, further comprising supplying chemicals to the supply tank from a supplemental supply tank.

19. The method of claim 17, further comprising:

controlling the amount of chemical supplied from the supply tank;

monitoring the amount of chemical supplied from the supply tank; and transmitting responses to the interrogation signal based upon the amount of chemical supplied from the supply tank.

20. The method of claim 17, further comprising:

modulating at least some of the interrogation signals to provide individual responder unit addressing;

demodulating the interrogation signals at each responder unit into a demodulated signal address;

comparing the demodulated signal address to an individual responder unit address at each responder unit; and enabling each responder unit to respond when the demodulated signal address matches the individual responder unit address.

* * * * *